(12) United States Patent
Karki et al.

(10) Patent No.: US 6,355,611 B1
(45) Date of Patent: Mar. 12, 2002

(54) SALT FORM OF A CONJUGATE USEFUL IN THE TREATMENT OF PROSTATE CANCER

(75) Inventors: Shyam B. Karki, Lansdale, PA (US); Mark Cameron, Bishops Stortford; David R. Lieberman, Barnet, both of (GB); Joseph E. Lynch, Plainfield, NJ (US); Michael A. Robbins, Short Hills, NJ (US); Yao-Jun Shi, Edison, NJ (US); Örn Almarsson, Shrewsbury, MA (US); Michael J. Kaufman, New Hope, PA (US); Maneesh J. Nerurkar, Herts (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/698,461

(22) Filed: Oct. 27, 2000

Related U.S. Application Data

(60) Provisional application No. 60/222,151, filed on Aug. 1, 2000, and provisional application No. 60/161,872, filed on Oct. 27, 1999.

(51) Int. Cl.⁷ .................. A61K 38/08; A61K 38/14; C07K 1/113; C07K 1/14; C07K 9/00
(52) U.S. Cl. .................. 514/8; 514/16; 530/322; 530/329; 530/344; 530/345
(58) Field of Search .................. 514/2, 8, 16, 17, 514/18, 34, 283; 530/300, 322, 328, 329, 330, 344, 345, 412, 417

(56) References Cited

U.S. PATENT DOCUMENTS

| | | | |
|---|---|---|---|
| 4,296,105 A | 10/1981 | Baurain et al. | 536/17 |
| 5,169,834 A | * 12/1992 | Arendt | 514/8 |
| 5,270,057 A | * 12/1993 | De Meere et al. | 424/499 |
| 5,346,907 A | * 9/1994 | Kerwin, Jr. et al. | 514/312 |
| 5,833,790 A | * 11/1998 | Heerze et al. | 424/185.1 |
| 5,866,679 A | 2/1999 | DeFeo-Jones et al. | 530/322 |
| 5,942,210 A | * 8/1999 | Ultee et al. | 424/1.69 |
| 5,948,750 A | 9/1999 | Garsky et al. | 514/2 |

FOREIGN PATENT DOCUMENTS

| | | | |
|---|---|---|---|
| WO | WO 96/05863 | | 2/1996 |
| WO | 98/18493 | * | 5/1998 |

OTHER PUBLICATIONS

G. M. Dubowchik et al., Monomethoxytrityl (MMT) as a Versatile Amino Protecting Group for Complex Prodrugs of Anticancer Compounds Sensitive to Strong Acids, Bases and Nucleophiles, Tetrahedron Letters, vol. 38, No. 30, pp. 5257–5260, 1997.

J. H. Beijnen et al., Aspects of the chemical stability of doxorubicin and seven other anthracyclines in acidic solution, Pharmaceutisch Weekblad Scientific Edition, vol. 7, pp. 109–116, 1985.

Ziad Abdeen et al., Degradation of Adriamycin in Aqueous Sodium Hydroxide: Formation of a Ring–A Oxabicyclononenone, J. Chem. Research (S), pp. 254–255, 1985.

J. H. Beijnen et al., Structure elucidation and characterization of daunorubicin degradation products, International Journal of Pharmaceutics, vol. 34, pp. 247–257, 1987.

J. H. Beijnen et al., Aspects of the degradation kinetics of doxorubicin in aqueous solution, International Journal of Pharmaceutics, vol. 32, pp. 123–131, 1986.

(List continued on next page.)

Primary Examiner—Jeffrey E. Russel
(74) Attorney, Agent, or Firm—David A. Muthard; Mark R. Daniel

(57) ABSTRACT

The present invention is directed to the sodium salt of formula 5:

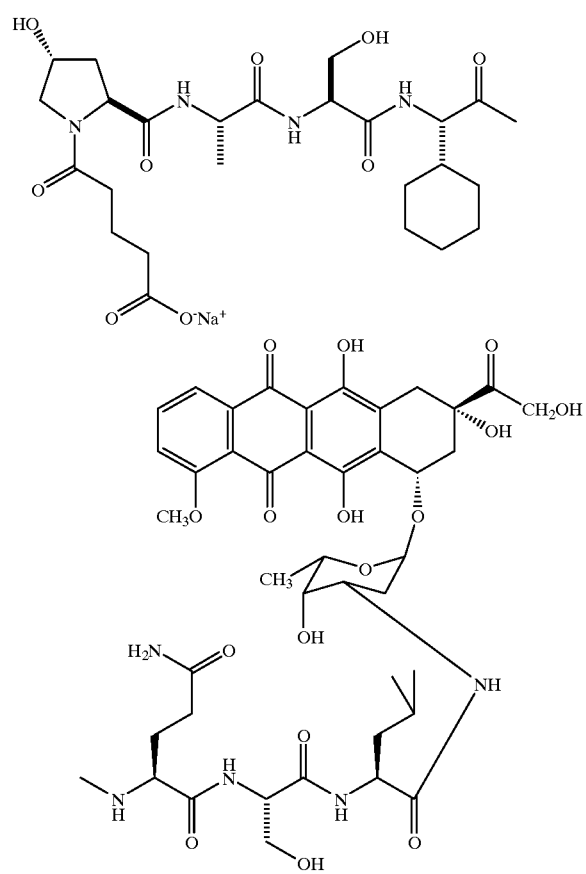

which may be useful in the treatment of prostate cancer and benign prostatic hyperplasia. Also described are lyophilized formulations that comprise the sodium salt 5 or the corresponding free acid.

31 Claims, No Drawings

K. Wassermann et al., Kinetics of the acid–catalyzed hydrolysis of doxorubicin, International Journal of Pharmaceutics, vol. 14, pp. 73–78, 1983.

J. H. Beijnen et al., Aspects of the degradation kinetics of daunorubicin in aqueous solution, International Journal of Pharmaceutics, vol. 31, pp. 75–82, 1986.

S. Eksborg, Reversed–Phase Liquid Chromatography of Adriamycin and Daunorubicin and Their Hydroxyl Metabolites Adriamycinol and Daunorubicinol, J. of Chromatography, vol. 149, pp. 225–232, 1978.

E. K. Nyhammar et al., Stability of doxorubicin hydrochloride and vincristine sulfate in two portable infusion–pump reservoirs, Am. J. Health–Syst. Pharm., vol. 53, pp. 1171–1173, May 1996.

V. Malatesta et al., Laser Photochemical Deglycosidation of Daunomycin and Adriamycin, Medecine Boilofie Environment, vol. 16, pp. 77–80, 1988.

M. J. Wood et al., Photodegradation of Doxorubicin, Daunorubicin and Epirubicin Measured by High–Performance Liquid Chromatography, Journal of Clinical Pharmacy and Therapeutics, vol. 15, pp. 291–300, 1990.

G. M. Rao et al., Electrochemical Studies of Antitumor Antibiotics, J. Electrochem. Soc., vol. 125, No. 4, pp. 534–539, Apr. 1978.

F. Arcamone, Daunomycin And Related Antibiotics, Antibiot. Chem., vol. 2, pp 109–115 & 191–195, 1978.

* cited by examiner

SEQUENCE LISTING

```
<160> NUMBER OF SEQ ID NOS:   4

<210> SEQ ID NO 1
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-(glutaryl)4-trans-hydroxy-L-proline
<221> NAME/KEY: VARIANT
<222> LOCATION: (4)...(4)
<223> OTHER INFORMATION: Xaa = cyclohexylglycine

<400> SEQUENCE: 1

Xaa Ala Ser Xaa Gln Ser Leu
 1               5

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa =
      4-(fluorenylmethoxyglutaryl)-4-trans-hydroxy-L-pro
```

```
          line
<221> NAME/KEY: VARIANT
<222> LOCATION: (4)...(4)
<223> OTHER INFORMATION: Xaa = cyclohexylglycine

<400> SEQUENCE: 2

Xaa Ala Ser Xaa Gln Ser Leu
 1               5

<210> SEQ ID NO 3
<211> LENGTH: 4
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = cyclohexylglycine
<221> NAME/KEY: VARIANT
<222> LOCATION: (4)...(4)
<223> OTHER INFORMATION: leucine benzylester

<400> SEQUENCE: 3

Xaa Gln Ser Leu
 1

<210> SEQ ID NO 4
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa =
      4-(fluorenylmethoxyglutaryl)-trans-hydroxy-L-proli
      ne
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: leucine benzylester

<400> SEQUENCE: 4

Xaa Ala Ser Xaa Gln Ser Leu
 1               5
```

SALT FORM OF A CONJUGATE USEFUL IN THE TREATMENT OF PROSTATE CANCER

RELATED APPLICATION

The present patent application claims the benefit of provisional applications Ser. No. 60/222,151, filed Aug. 1, 2000, and Ser. No. 60/161,872, filed Oct. 27, 1999, both of which were pending on the date of the filing of the present application.

BACKGROUND OF THE INVENTION

In 1999 new cases of cancer of the prostate gland were expected to be diagnosed in 179,300 men in the U.S. and 37,000 American males were expected to die from this disease (Landis, S. H. et al. *CA Cancer J. Clin.* 49:8–31 (1999)). Prostate cancer is the most frequently diagnosed malignancy (other than that of the skin) in U.S. men and the second leading cause of cancer-related deaths (behind lung cancer) in that group.

Compositions useful in the treatment of prostatic cancer and related conditions are described in U.S. Pat. No. 5,948,750, issued Sep. 7, 1999 (corresponding to PCT Publ.No. WO 98/18493). Said compositions comprise chemical conjugates comprising known cytotoxic agents and oligopeptides having amino acid sequences that are selectively proteolytically cleaved by free prostate specific antigen and that include a cyclic amino acid having a hydrophilic substituent. The oligopeptide moieties are selected from oligomers that are selectively recognized by free prostate specific antigen (PSA) and are capable of being proteolytically cleaved by the enzymatic activity thereof.

Ideally, the cytotoxic activity of the cytotoxic agent is greatly reduced or absent when the intact oligopeptide containing the PSA proteolytic cleavage site is bonded directly, or through a chemical linker, to the cytotoxic agent. Also ideally, the cytotoxic activity of the cytotoxic agent increases significantly, or is restored completely, upon proteolytic cleavage of the attached oligopeptide at the cleavage site. Anthracycline antibiotics, in particular doxorubicin, are among the cytotoxic agents that were described in the published patent applications as preferably incorporated into such conjugates, which may be referred to as PSA conjugates. The PSA conjugates that incorporate doxorubicin that have been previously described incorporate the oligopeptide on the amine moiety of the sugar residue of doxorubicin.

Those oligopeptides preferably incorporate a N-terminus protecting group to prevent or reduce proteolysis of the oligopeptide by non-PSA enzymes.

Among the preferred N-terminus protecting groups that are incorporated onto a PSA conjugate are the dicarboxylic acid alkanes, such as succinyl, glutaryl and the like. One of the preferred compounds described in U.S. Ser. No. 08/950,805, now U.S. Pat. No. 5,948,750 (PCT Publ.No. WO 98/18493) incorporating such an N-terminus protecting group is the compound of Formula 4:

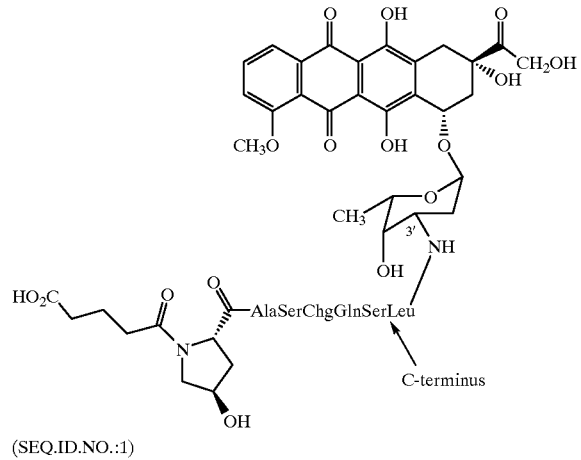

(SEQ.ID.NO.:1)

It is the object of this invention to provide a salt form of Compound 4 which is characterized by properties that offer advantages in the preparation, handling, storage and delivery of the compound to a patient in need of anti-cancer treatment.

It is the further the object of this invention to provide a stable lyophilized formulation of Compound 4 which is characterized by properties that offer advantages in the storage of the compound and delivery of the compound to a patient in need of anti-cancer treatment.

SUMMARY OF THE INVENTION

A sodium salt of a PSA conjugate compound having the formula 5 is disclosed:

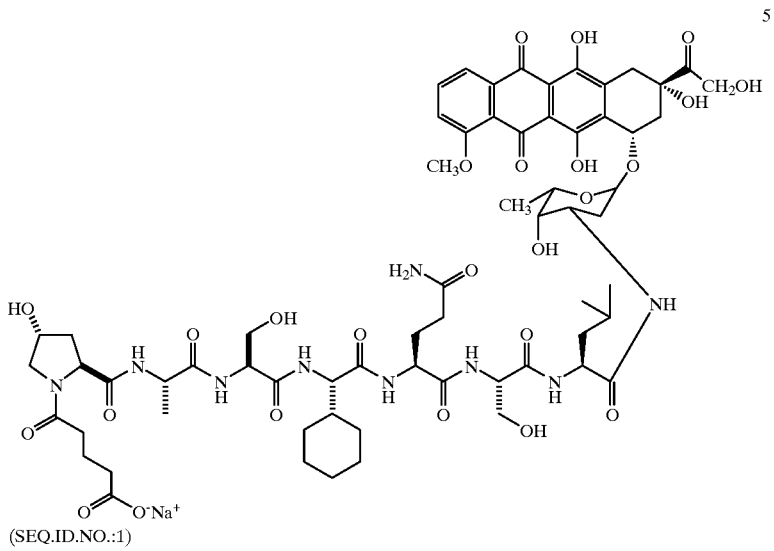

(SEQ.ID.NO.:1)

Such a salt is useful in the treatment of prostate cancer and benign prostatic hyperplasia (BPH).

Also described are formulations that comprise the salt of the invention and methods of preparing the salt.

DETAILED DESCRIPTION OF THE INVENTION

The present invention is directed to the sodium salt of the formula 5:

tetracyclic doxorubicinone moiety is more readily cleaved at aqueous pH of less than 4.0. Therefore the sodium salt offers clear formulation advantages over the free acid, which has an unbuffered aqueous pH of less than 4.0.

It has further been discovered that the sodium salt of the Formula 5 offers advantages with respect to dissolution in water. The solubility of the sodium salt of the Formula 5 at room temperature is greater than 277 mg/mL of water. The solubility of the free acid (Compound 4) is 13.8 mg/mL of water at room temperature. It has also been surprisingly

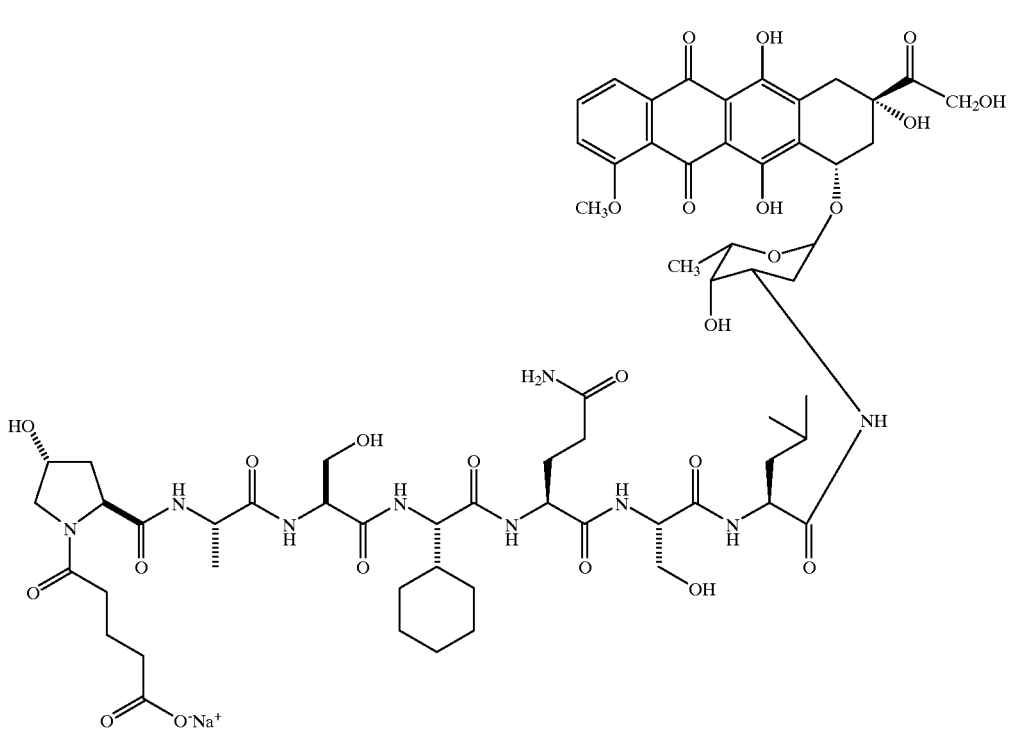

5

(SEQ.ID.NO.:1)

It has been surprisingly discovered that the sodium salt of a PSA conjugate compound, which is specifically described as the free acid in Example 4 of PCT Publ. No. WO 98/18493, is characterized by several advantageous physical properties when compared to the previously described free acid form (formula 4 hereinabove).

In particular, the sodium salt is crystalline and can be precipitated from an aqueous solution by the addition of a water miscible organic solvent. Such water miscible solvents include, but are not limited to tetrahydrofuran, methanol, ethanol, isopropanol and acetone. Preferably, acetone is utilized to precipitate the salt from solution. The crystalline nature of the sodium salt also allows for the purification of large quantities of the compound by recrystallization. Purification of the previously disclosed free acid requires the use of chromatographic techniques and freeze drying/lyophilization that are not amenable to large scale preparations which are often associated with commercial pharmaceutical agents.

It has also been surprisingly discovered that the sodium salt compound of the Formula 5 is more thermally stable than the corresponding free acid compound (Formula 4). An aqueous solution of the sodium salt of the instant invention has a pH of greater than 5.0. It has been discovered that the bond between the sugar moiety of doxorubicin and the found that the sodium salt of the Formula 5 dissolves in water without forming aggregates, such as those that have been observed for the free acid. It has been found that the formation of aggregates hinders the filtration of an aqueous solution of the free acid compound through a $0.22\mu$ filter, which is used to sterilize the aqueous solution prior to administration.

The instant invention is also directed to the process for the preparation of the salt of the Formula 5 which comprises the step of treating the acid of the Formula 4 with a base. The bases that may be used in the preparation of the salt of the Formula 5 include, but are not limited to: NaOH, $Na_2CO_3$, sodium acetate, sodium citrate (citric acid, trisodium salt) and the like. The preferred base is NaOH.

The instant invention is further directed to an alternative process for the preparation of the salt of the Formula 5 which comprises the step of treating the piperidine salt of the acid of the Formula 4 with a base. The bases that may be used in this preparation of the salt of the Formula 5 include, but are not limited to: NaOH, $Na_2CO_3$, sodium acetate, sodium citrate and the like. The preferred base is sodium acetate.

The instant invention is also directed to an second alternative process for the preparation of the salt of the Formula 5 which comprises the steps of a) treating the intermediate of the Formula 3

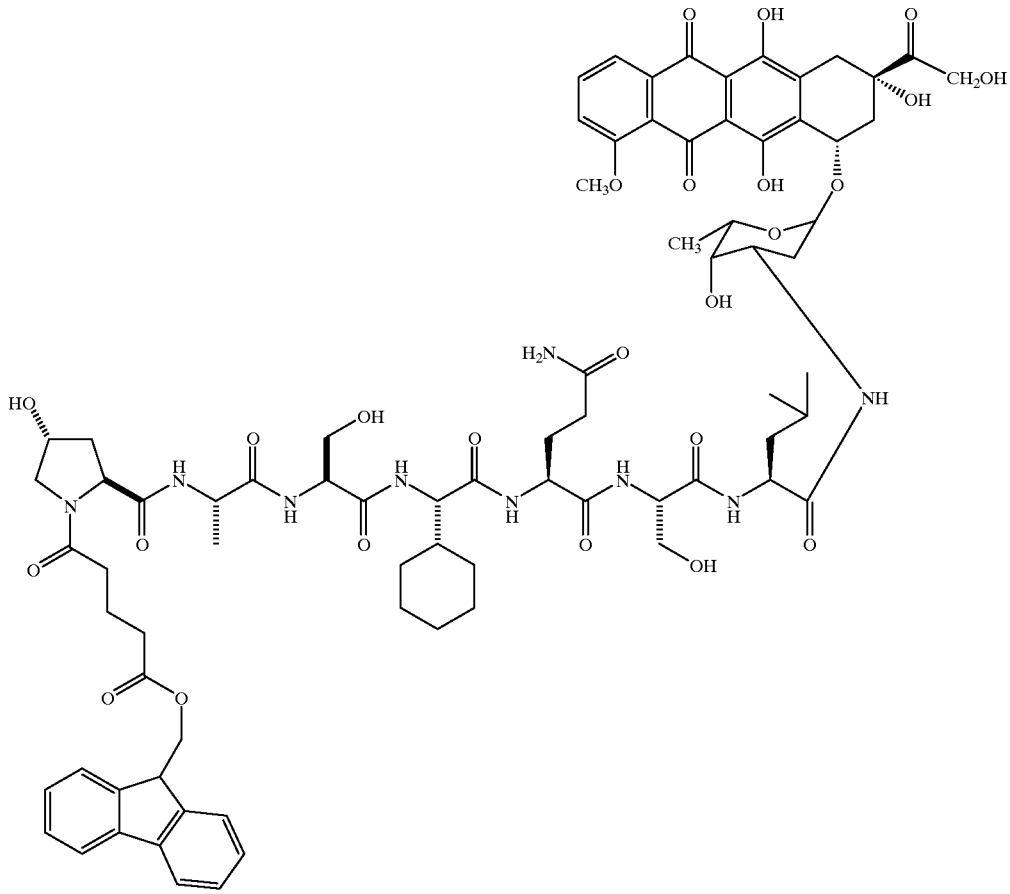

(SEQ.ID.NO.:2)

with piperidine to provide a resulting mixture; b) treating the resulting mixture with an acid to provide a second resulting mixture; and c) treating the second resulting mixture with a base. The bases that may be used in this preparation of the salt of the Formula 5 include, but are not limited to: NaOH, $Na_2CO_3$, sodium acetate, sodium citrate and the like. The preferred base is sodium acetate. The acid that may be used in this preparation of the salt of the Formula 5 include, but are not limited to: hydrochloric acid and acetic acid. The preferred acid is acetic acid.

In an embodiment of the instant process, the process further comprises the step of precipitating the sodium salt of the Formula 5 from the resulting aqueous solution by adding a water miscible organic solvent to the solution. Such water miscible solvents include, but are not limited to, tetrahydrofuran, isopropanol and acetone. Preferably, acetone is utilized to precipitate the salt from solution.

In another embodiment of the instant process, the process further comprises the step of isolating the salt of the Formula 5 from the resulting aqueous solution by evaporating the solvent.

It has been surprisingly discovered that a lyophilized formulation of the PSA conjugate compound 4, which is specifically described in Example 4 of PCT Publ.No. WO 98/18493, is characterized by several advantageous physical properties when compared to the previously described free acid.

In particular, the lyophilized formulation is prepared by the addition of a salt of a carboxylic acid to an aqueous solution of the previously described free acid compound 4. The amount of carboxylate salt that is added to the prelyophilization solution of the compound of formula 4 is from about 3 molar equivalents of base of trisodium citrate per mole of compound 4 to about 9 molar equivalents of base per mole of compound 4. Preferably, the amount of salt that is added is about 5 molar equivalents of base per mole of compound 4. Lyophilization of this buffered solution provides a water-soluble solid that has improved storage stability.

Among the salts of a carboxylic acid that may be used to prepare the lyophilized formulation of the free acid compound 4 include but is not limited to: acetate, ascorbate, benzoate, citrate, formate, fumarate, lactate, maleate, malate, succinate tartarate-α and tartarate-m. Preferably the salt of carboxylic acid that is used is selected from citrate, succinate, tartrate-α and tartrate-m. The counterion of the salt may be sodium, potassium, lithium or calcium. Preferably, trisodium citrate is used to prepare the lyophilized formulation with the free acid compound 4. The amount of trisodium citrate that is added to the prelyophilization solution of the compound of formula 4 is from about 1 mole (3 molar equivalents of base) of trisodium citrate per mole of compound 4 to about 3 moles (9 molar equivalents) of trisodium citrate per mole of compound 4. Preferably, the amount of sodium citrate that is added is about 1.66 moles per mole of compound 4. Lyophilization of this buffered solution provides a water-soluble solid that is improved storage stability.

Alternatively, the lyophilized formulation is prepared by the addition of carboxylate/carboxylic acid buffer to an aqueous solution of the sodium salt compound 5, prior to lyophilization. Preferably, such a buffer comprises trisodium citrate/citric acid buffer, disodium succinate/succinic acid or sodium tartrate/tartaric acid. More preferably, the buffer comprises trisodium citrate/citric acid buffer. Preferably, the concentration of the sodium citrate/citric acid buffer is from about 10 mM to about 100 mM. More preferably, the concentration of the sodium citrate/citric acid buffer is from about 40 mM to about 60 mM. Preferably, the sodium citrate/citric acid buffer is from about pH 5.0 buffer to about pH 6.0 buffer.

It has been surprisingly discovered that the buffered formulation of the instant invention is more thermally stable than the lyophilized free acid compound of Formula 4, the crystalline salt compound 5 or an aqueous solution of either the free acid or salt compound. It has also been surprisingly discovered that the reconstituted solution of the lyophilized formulation of the instant invention is also more thermally stable than the aqueous solution of the free acid compound or the aqueous solution of the sodium salt compound 5.

It is preferred that the prelyophilization solution of either the PSA conjugate compound 4 or the salt compound 5 be at a pH that is from about 5.0 to about 6.0. More preferably, the pH of the prelyophilization solution is at a pH of from about 5.5 to about 6.0. Most preferably, the prelyophilization solution is at a pH of about 5.7. In order to maintain the prelyophilization solution at a preferred pH, an acid and/or a base is added to the buffered solution of compound 5 or compound 4. Preferably the acid that is added to the buffered solution is about 0.1 N HCl. Preferably, the base that is added to the buffered solution is about 0.1 N NaOH.

It has further been discovered that the lyophilized formulation offers advantages with respect to dissolution in water. The solubility of the free acid compound 4 at room temperature is directly dependent on the pH of the solution, from 3.98 mg/mL at pH 2.35 to greater than 156 mg/mL of water at pH 5.72.

It has also been surprisingly found that the instant lyophilized formulation dissolves in water without forming aggregates, such as those that have been observed for the free acid. It has been found that the formation of aggregates hinders the filtration of an aqueous solution of the free acid compound through a 0.22µ filter, which is used to sterilize the aqueous solution that is administered in the clinical setting.

It has also been discovered that addition of a sugar to the prelyophilization solution used to prepare the lyophilized formulation of the instant invention increases the stability of the lyophilized formulation and provides for a product having a longer pharmaceutical shelf-life. The added sugar may also act as a bulking agent and help reduce the hygroscopicity of the formulation. Thus, the instant formulation optionally further comprises a sugar, which is selected from glucose, mannitol, lactose, sucrose, fructose and the like. Preferably, the instant lyophilized formulation further comprises sucrose. Preferably the amount (in moles) of the sugar added to the prelyophilization solution used to prepare the lyophilized formulation is from about 2 times the amount (in moles) of compound 4 to about 20 times the amount (in moles) of compound 4 or compound 5. More preferably, the amount (in moles) of the sugar added to the prelyophilization solution used to prepare the lyophilized formulation is from about 5 times the amount (in moles) of compound 4 or compound 5 to about 15 times the amount (in moles) of compound 4 or compound 5.

The following abbreviations are utilized in the specification and tables to denote the indicated amino acids and moieties:

| | |
|---|---|
| TFA: | trifluoroacetic acid |
| AA: | acetic acid |
| 4-Hyp | 4-hydroxyproline |
| Boc/BOC | t-Butoxycarbonyl; |
| Chg | cyclohexylglycine |
| DMA | dimethylacetamide |
| DMF | Dimethylformamide; |
| DMSO | dimethyl sulfoxide; |
| EDC | 1-(3-dimethylaminopropyl)-3-ethyl-carbodiimide hydrochloride; |
| EtOAc | Ethyl acetate; |
| EtOH | Ethanol; |
| FAB | Fast atom bombardment; |
| HOAt | 1-Hydroxy-7-azabenzotriazole |
| HOBt | 1-Hydroxybenzotriazole hydrate; |
| HOPO | 2-hydroxypyridine-N-oxide |
| HPLC | High-performance liquid chromatography; |
| IPAc | isopropylacetate |
| MeOH | methanol |
| RPLC | Reverse Phase Liquid Chromatography |
| THF | Tetrahydrofuran. |

The PSA conjugate lyophilized formulation of the invention may additionally comprise pharmaceutically acceptable carrier, excipient or diluent. In this regard, see, e.g. *Remington's Pharmaceutical Sciences*, 16th ed., 1980, Mack Publishing Company, edited by Osol et al. Such compositions may include proteins, such as serum proteins, for example, human serum albumin, and the like. Suitable diluents for reconstituting the lyophilized formulation prior to administration may include, for example, sterile water, isotonic saline, dilute aqueous dextrose, a polyhydric alcohol or mixtures of such alcohols, for example, glycerin, propylene glycol, polyethylene glycol and the like. As used, "pharmaceutically acceptable" refers to those agents which are useful in the treatment or diagnosis of a warm-blooded animal including, for example, a human, equine, porcine, bovine, murine, canine, feline, or other mammal, as well as an avian or other warm-blooded animal. The preferred mode of administration of the reconstituted formulation is parenterally, particularly by the intravenous, intramuscular, subcutaneous, intraperitoneal, or intralymphatic route.

As used herein, the terms "composition" and "formulation" are intended to encompass a product comprising the specified ingredients, as well as any product which results, directly or indirectly, from combination of the specific ingredients.

The formulation of the instant invention may also be administered in combination with an inhibitor of prenyl-protein transferase, in particular farnesyl-protein transferase.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The salt of the invention is effective over a wide dosage range depending on factors such as the disease state to be treated or the biological effect to be modified, the manner in which the conjugate salt is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made and are meant to be

EXAMPLE 1

Preparation N-(N'-(Fm-Glutaryl)-trans-4-hydroxy-L-prolinyl-alanyl)serine

Step 1: N-Boc-trans-4-hydroxy-L-proline

A solution of trans-4-hydroxy-L-proline (3.0 kg, 22.88 M) in 1 M aqueous sodium hydroxide (25.2 L) and tert-butanol (12.0 L) was treated with a solution of di-tert-butyldicarbonate (5.09 kg) in tert-butanol (6.0 L) at 20° C. over 20 minutes. Upon complete addition, the resulting solution was stirred at 20° C. for 2 hours. The solution was extracted with hexane (2×15.0 L) and then acidified to pH 1 to 1.5 by cautious addition of a solution of potassium hydrogen sulphate (3.6 kg) in water (15.0 L). The mixture was extracted with ethyl acetate (3×15.0 L). The combined ethyl acetate extracts were washed with water (2×1.0 L) and dried by azeotropic distillation at atmospheric pressure (final KF of ethyl acetate solution <0.1%).

The ethyl acetate solution was then concentrated by atmospheric distillation to a volume of 15.0 L, diluted with hexane (8.0 L), seeded and stirred at 20° C. for 1 hour. Hexane (22.5 L) was added over 2 hours, the slurry was cooled to 0° C. for 1 hour and the solid collected by filtration. The product was washed with cold (0° C.) 2:1 hexane/ethyl acetate (15.0 L) and dried in vacuo at 45° C. to afford the title compound as a white crystalline solid.

Step 2: N-Boc-trans-4-hydroxy-L-proline Pentafluorophenyl ester

Boc-trans-4-hydroxy-L-proline (3.5 kg) (prepared as described in Step 1) and pentafluorophenol (3.06 kg) were dissolved in ethyl acetate (52 L). The solution was treated with a solution of dicyclohexylcarbodiimide (3.43 kg) in ethyl acetate (8 L) and the mixture was stirred at room temperature for 2 hours. The resulting slurry was cooled to 0° C., filtered and the solids washed with ethyl acetate (15 L). The filtrate was evaporated at atmospheric pressure to a volume of 10 L and diluted with hexane (100 L). The resulting mixture was stirred at room temperature overnight and then cooled to 0° C. for 1 hour. The solid was collected by filtration, washed with cold (° C.) 10:1 hexane/ethyl acetate (15 L) and dried at 45° C. in vacuo to afford the title compound as a white crystalline solid.

Step 3: N-(trans-4-hydroxy-L-prolinyl-alanyl)serine hydrochloride

N-alanylserine (1.5 kg, 8.515 M) and Boc-trans-4-hydroxy-L-proline (3.72 kg) (prepared as described in step 2) were heated at 50° C. in dimethylformamide (15 L) for 3 hours. The solution was cooled to 20° C., treated with concentrated hydrochloric acid (7.5 L) and stirred at room temperature for 24 hours. The resulting slurry was diluted with isopropanol (30 L), stirred at room temperature for 30 minutes and then cooled to 0° C. for 1 hour. The solid was collected by filtration and washed with isopropanol (20 L). The solid was dried in vacuo at 40° C. to afford the title compound as a white crystalline solid.

Step 4: Fluorenylmethyl Glutarate

9-Fluorenyl methanol (2.0 kg), glutaric anhydride (2.33 kg) and sodium bicarbonate (1.71 kg) were stirred together in N-methylpyrrolidinone (8.0 L) at room temperature for 72 hours. The slurry was filtered and the solids washed with isopropyl acetate (2×10.0 L). The filtrate was washed with 1.0 M hydrochloric acid (3×10.0 L). The organic layer was extracted with 1.0 M aqueous sodium hydroxide (3×8.0 L). The combined basic extracts were covered with isopropyl acetate (20.0 L) and acidified to pH 2 with 2.0 M hydrochloric acid (12.5 L). The phases were separated and the aqueous phase was extracted with isopropyl acetate (10.0 L).

The combined organic phases were washed with water (10.0 L) and dried by azeotropic distillation at <60° C. under reduced pressure (KF<0.05%). The solution was then concentrated under reduced pressure (<60° C.) to a volume of 7.0 L. The solution was diluted with hexane (6.0 L), seeded and stirred at room temperature for 30 minutes. The resulting slurry was diluted by addition of hexane (42.0 L) over 40 minutes. The slurry was cooled to 0° C. for 1 hour and the solid collected by filtration and washed with cold (0° C.) 8:1 hexane/iPAc (20.0 L). The solid was dried in vacuo at 45° C. to afford the title compound as a pale cream solid.

Step 5: Fluorenylmethyl Glutarate Pentafluorophenyl Ester

Fluorenylmethyl glutarate (2.5 kg) (prepared as described in Step 4) and pentafluorophenol (1.63 kg) were dissolved in ethyl acetate (25 L). The solution was treated with a solution of dicyclohexylcarbodiimide (1.83 kg) in ethyl acetate (7.5 L) and the mixture was stirred at 20° C. overnight. The resulting slurry was filtered and the solids were washed through with ethyl acetate (10 L). The filtrate was evaporated at atmospheric pressure to a volume of 7.5 L and diluted with hexane (75 L). The slurry was filtered at 60–65° C. then allowed to cool to room temperature and stirred overnight. The slurry was cooled to 0° C. for 1 hour, the solid collected by filtration and washed with 10:1 hexane/ethyl acetate (15 L). The solid was dried in vacuo at 45° C. to afford the title compound as a white crystalline solid.

Step 6: N-(N'-(Fm-Glutaryl)-trans-4-hydroxy-L-prolinyl-alanyl)serine

N-(trans-4-hydroxy-L-prolinyl-alanyl)serine hydrochloride (2.3 kg) (prepared as described in Step 3) was suspended in dimethylformamide (22 L) and the slurry was treated with N-ethylmorpholine (911 ml) followed by a solution of fluorenylmethyl glutarate pentafluorophenyl ester (3.5 kg) (prepared as described in Step 5) in dimethylformamide (14 L). The mixture was heated at 50° C. for 3 hours and the resulting solution evaporated to residue under reduced pressure. The residue was partitioned between water (80 L) and tert-butyl methyl ether (34 L). The phases were separated and the aqueous layer was extracted with tert-butyl methyl ether (34 L). The aqueous solution was seeded and stirred at room temperature overnight. The solid was collected by filtration (slow) and washed with water (25 L). The damp filter cake was dissolved in isopropanol (90 L) with warming and the solution concentrated to half volume by distillation at atmospheric pressure. Additional portions of isopropanol (3×45 L) were added and the batch was concentrated to ca half volume by atmospheric distillation after addition of each portion (Final KF of liquors <0.5%). The slurry was diluted with isopropanol (23 L), stirred at 20° C. overnight, cooled to 0° C. for 1 hour and the solid collected by filtration. The cake was washed with isopropanol (20 L) and the solid dried in vacuo at 45° C. to afford the crude product as a white solid.

Step 7: Recrystallisation of N-(N'-(Fm-Glutaryl)-trans-4-hydroxy-L-prolinyl-alanyl)serine N-(N'-(Fm-Glutaryl)-trans-4-hydroxy-L-prolinyl-alanyl)serine (3.4 kg) (prepared as described in Step 6) was dissolved in methanol (51 L) at reflux. The solution was filtered and concentrated by atmospheric distillation to a volume of 17 L (5 ml/g). The solution was diluted with ethyl acetate (102 L) allowed to cool to 20° C. and stirred overnight. The resulting slurry was cooled to 0° C. for 1 hour and the solid was collected by filtration. The cake was washed with cold (0° C.) 10:1 ethyl acetate/methanol (20 L) and dried in vacuo at 45° C. to afford the product as a white solid.

EXAMPLE 2

Preparation N-(cyclohexylglycyl-glutaminyl-serinyl) leucine benzyl ester hydrochloride (SEQ.ID.NO.: 3)

Step 1: N-(serinyl)leucine benzyl ester hydrochloride

Leucine benzyl ester p-tosylate (1000 g) and HOBt (412 g) were slurried in isopropyl acetate (12 L). The mixture was cooled to 0° C. in an ice-bath and a slurry of sodium bicarbonate (469.7 g) in water (1 L), N-BOC-L-serine (573.6 g) in water (2 L) and EDC.HCl (560.2 g) in water (2 L) were added. The mixture was allowed to warm to 20° C. over 30 minutes and aged at 20° C. for 2 hours (<1 A % Leu-OBn remaining). If the reaction was not complete after 2 hours, further NaHCO$_3$ and EDC.HCl were added. The phases were separated and the organic layer was washed sequentially with saturated sodium bicarbonate (2×3.75 L), 0.5 M sodium hydrogen sulphate (2×3.75 L) and water (2×2.5 L).

The wet, isopropyl acetate solution was concentrated under reduced pressure to 3 L and the water content checked. (KF=0.12%. It is important that this solution is dry prior to the addition of hydrogen chloride in isopropyl acetate). The solution was transferred to a 20 L round bottom flask under a nitrogen atmosphere and cooled to 0° C. To the solution was added 3.6 M HCl in isopropyl acetate (7 L, 10 mol equiv. HCl). The product began to crystallize after 5 minutes. The reaction was aged at 0° C. for 1 hr, and then allowed to warm to room temperature.

The slurry was cooled to 0–5° C., diluted with heptane (2.5 L) and aged at 0° C. for 30 minutes. The product was collected by filtration, washed with cold isopropyl acetate/heptane (4:1) (2.5 L) and dried in vacuo at 35° C., with a nitrogen sweep.

Step 2: N-(N'-(Boc)-glutaminyl-serinyl)leucine benzyl ester

N-(serinyl)leucine benzyl ester hydrochloride (350 g) (prepared as described in Step 1), HOBt (157.7 g) and N-Boc-L-glutamine (262.5 g) were slurried in DMF (2.5 L) and the mixture was cooled to 0° C. N-Ethylmorpholine (245.5 g) and EDC.HCl (214 g) were added and the mixture was aged at 0° C. for 2.5 hours. Water (14.7 L) was added over 20 minutes and the white slurry aged at 0° C. for 1 hour. The product collected by filtration and washed with water (3.2 L). The cake was dried in the fume-hood overnight. The isolated N-BOC-Gln-Ser-Leu-OBn, which contained DMF and HOBt, was combined with a second batch of identical size, and swished in water (12 L) at 20° C. for 1 hour. The product was collected by filtration, washed with water (2.5 L) and air-dried in a fume-hood over the weekend. The batch was dried in vacuo, at 42° C., with a nitrogen bleed.

Step 3: N-(glutaminyl-serinyl)leucine benzyl ester hydrochloride

N-(N'-(Boc)-glutaminyl-serinyl)leucine benzyl ester (715 g, 1.33 M) (prepared as described in Step 2) was suspended in iPAc (3.5 L) at room temperature. To the slurry was added a 3.8 M solution of HCl in iPAc (3.5 L, 13.3 M) whereupon all the solids dissolved. After a short time, the product crystallized. The mixture was stirred at room temperature for 3.75 hours when HPLC showed complete reaction. The slurry was diluted with iPAc (4.0 L), stirred for 1 hour at room temperature and the solid collected by filtration under nitrogen. The product is very hygroscopic in the presence of excess HCl and must be collected under dry nitrogen.

The cake was washed with iPAc (4.0 L), the solid dried on the filter under nitrogen for 2 hours and then dried in vacuo at 45° C.

Step 4: N-(N'-(Boc)-cyclohexylglycylglutaminyl-serinyl)leucine benzyl ester(SEQ.ID.NO.: 2)

N-(glutaminyl-serinyl)leucine benzyl ester hydrochloride (2.6 kg) (prepared as described in Step 3), N-Boc-L-cyclohexylglycine (1.414 kg) and HOBt hydrate (168 g) were dissolved in DMF (13.0 L). N-ethylmorpholine (1.266 kg, 11.0 M) and EDC hydrochloride (1.265 kg) were added and the mixture stirred at 20° C. for 3 hours. The solution was diluted with ethyl acetate (13.0 L) and water (26.0 L) added. The product precipitated and the slurry was stirred at room temperature for 1 hour. The solid was collected by filtration, washed with 1:1 ethyl acetate/water (60 L) dried on the filter under nitrogen for 24 hours and dried in vacuo at 45°. The title compound was obtained as a white solid.

Step 5: N-(cyclohexylglycyl-glutaminyl-serinyl) leucine benzyl ester hydrochloride (SEQ.ID.NO.: 2)

N-(N'-(Boc)-cyclohexylglycylglutaminyl-serinyl)leucine benzyl ester (SEQ ID NO:3) (1850 g) (prepared as described in Step 4) was slurried in isopropyl acetate (3.2 L). The slurry was cooled to 0° C. in an ice bath and 3.8 M HCl/isopropyl acetate (3.7 L, 11.4 mol equiv.) was added over 5 minutes, maintaining the temperature between 8 and 10° C. The starting material had dissolved after 15–20 minutes. The solution was seeded and the reaction aged at 8–10° C. for 2 hrs, (<1 A % N-Boc-tetrapeptide-OBn remaining). The batch was filtered, under a nitrogen blanket, washed with cold (10° C.) isopropyl acetate (4×3 L) then dried on the filter under nitrogen. The solid was dried in vacuo, at 40° C.

The crude N-(cyclohexylglycyl-glutaminyl-serinyl) leucine benzyl ester (SEQ ID NO:3) hydrochloride (2.2 Kg) was slurried in methanol (22.3 L) at room temperature. The batch was stirred for 1 hour and then ethyl acetate (44.6 L) was added over 30 minutes. The batch was cooled to 0–5° C., aged for one hour, then filtered and washed with cold (0–5° C.) methanol/ethyl acetate (6 L, 1:2). The solid was dried on the filter, under nitrogen, for 45 minutes and then dried in vacuo, at 40° C., with a nitrogen sweep.

The N-(cyclohexylglycyl-glutaminyl-serinyl)leucine benzyl ester (SEQ ID NO:3) hydrochloride (1.478 Kg) was slurried in methanol (14.8 L) at room temperature and the batch stirred for 1 hr. Ethyl acetate (29.6 L) was added over 30 minutes, the batch was cooled to 0–5° C. and aged for an hour. The solid collected by filtration, washed with cold (0–5° C.) methanol/ethyl acetate (4.5 L, 1:2), dried on the filter for 45 minutes, under nitrogen, and then dried under vacuum, at 40° C. This material was then utilized in subsequent reactions.

EXAMPLE 3

Preparation N-(N'-(Fm-Glutaryl)-trans-4-hydroxy-L-prolinyl-alanyl-serine-cyclohexylglycyl-glutaminyl-serinyl)leucine (Compound 1) (SEQ.ID.NO.: 2)

Step 1: N-(N'-(Fm-Glutaryl)-trans-4-hydroxy-L-prolinyl-alanyl-serine-cyclohexylglycyl-glutaminyl-serinyl)leucine benzyl ester (SEQ.ID.NO.: 4)

N-(cyclohexylglycyl-glutaminyl-serinyl)leucine benzyl ester (SEQ ID NO:3) hydrochloride (500 g) (prepared as described in Example 2), N-(N'-(Fm-Glutaryl)-trans-4-hydroxy-L-prolinyl-alanyl)serine (490 g) (prepared as described in Example 1) and HOAt (160 g) were slurried in DMF (8.2 L) and cooled to 2° C. in an ice bath. N-ethylmorpholine (135 ml) was added followed by EDC.HCl (210 g). The mixture was stirred at 0–2° C. for 2 hours and sampled. HPLC showed 0.2 A % tetrapeptide remaining. The reaction mixture was diluted with ethyl acetate (4 L) and transferred to a 30-gallon glass vessel through a 5µ in-line filter. The flask and lines were rinsed with ethyl acetate/DMF (1:1, 500 ml) and ethyl acetate (4 L). Water (16.4 L) was added over 25 minutes (temperature 11° C. to 23° C.) and the mixture stirred slowly, at 20° C., for 30 minutes. The product was collected by filtration, washed with water (3 L), ethyl acetate (1 L) and water (2×3 L), then dried on the filter under nitrogen, and dried in vacuo at 45° C.

Alternate Step 1: Fm-Glutaryl-Hyp-Ala-Ser-Chg-Gln-Ser-Leu-O-benzyl (SEQ.ID.NO.: 4)

HCl.H-Chg-Gln-Ser-Leu-OBn (SEQ ID NO:3) (100 g), Fm-Glutaryl-Hyp-Ala-Ser-OH (98 g) and 4-hydroxypyridine-N-oxide (HOPO, 18.2 g) were slurried in DMF (1.6 L) and cooled to 2° C. in an ice bath. N-ethylmorpholine (27 ml) was added followed by EDC.HCl (42 g). The mixture was stirred at 2–5° C. for 4 hours and sampled. HPLC showed 0.6 A % tetrapeptide remaining. The reaction mixture was diluted with ethyl acetate (1.64 L), water (3.3 L) was added over 70 minutes and the mixture stirred slowly, at 20° C., for 60 minutes. The product was collected by filtration, washed with water (1.5 L), ethyl acetate (1 L) and water (3×1 L), then dried on the filter under nitrogen, and dried in vacuo at 45° C.

Step 2: N-(N'-(Fm-Glutaryl)-trans-4-hydroxy-L-prolinyl-alanyl-serine-cyclohexylglycyl-glutaminyl-serinyl)leucine (SEQ.ID.NO.: 2)

N-(N'-(Fm-Glutaryl)-trans-4-hydroxy-L-prolinyl-alanyl-serine-cyclohexylglycyl-glutaminyl-serinyl)leucine benzyl ester (SEQ ID NO:4) (1.1 Kg) (prepared as described in Step 1) was dissolved in dimethylacetamide (7.8 L) containing methanesulphonic acid (93.5 ml). 5% Pd/C (110 g, 10 wt %), slurried in DMA (1.0 L), was added and the mixture hydrogenated at atmospheric pressure for 1 hour 40 minutes. The reaction mixture was sampled: HPLC showed no starting material remaining.

The reaction mixture was filtered through a pre-wetted (DMA) pad of hyflo (500 g) to remove the catalyst. The hyflo pad washed with DMA (2.2 L) and then ethyl acetate (5.5 L). The filtrate was diluted with ethyl acetate (5.5 L) and stirred for 15 minutes. Water (44 L) was added over 40 minutes and the batch age for 1 hour. The solid collected by filtration, washed with water (1×10 L, 3×20 L), dried on the filter under a nitrogen blanket and dried in vacuo at 45° C.

Alternate Step 2: N-(N'-(Fm-Glutaryl)-trans-4-hydroxy-L-prolinyl-alanyl-serine-cyclohexylglycyl-glutaminyl-serinyl)leucine (SEQ.ID.NO.: 2)

Fm-Glutaryl-Hyp-Ala-Ser-Chg-Gln-Ser-Leu-OBn (SEQ ID NO:4) (prepared as described in Step 1 or Alternate Step 1) (200 g) was dissolved in dimethylacetamide (1.9 L) at 45–50° C. 5% Pd/C (20 g, 10 wt %) slurried in DMA (100 ml) was added and the slurry was cooled to −5 to −10° C. The mixture was hydrogenated at atmospheric pressure maintaining the temperature between −10 and −5° C. for 5.5 hours.

The mixture was filtered while cold through a pre-wetted pad of Hyflo. The filtrate was diluted with ethyl acetate (2.5 L) and water (8.0 L) was added. The batch was aged for a further 1 hour and the solid was collected by filtration. The cake was washed with water and sucked down on the filter and then dried in vacuo at 45° C. with a nitrogen sweep.

Step 3: N-(N'-(Fm-Glutaryl)-trans-4-hydroxy-L-prolinyl-alanyl-serine-cyclohexylglycyl-glutaminyl-serinyl)leucine (SEQ ID NO:2) Swish Purification Crude N-(N'-(Fm-Glutaryl)-trans-4-hydroxy-L-prolinyl-alanyl-serine-cyclohexylglycyl-glutaminyl-serinyl)leucine (SEQ ID NO:2) (2.58 kg) (prepared as described in Step 2 or Alternative Step 2) was sieved.

The solid (2.56 Kg) was swished in ethyl acetate for 3 hours. The solid was collected by filtration, washed with ethyl acetate (26 L), dried on the filter under nitrogen and dried in vacuo at 40° C. The product was analyzed for purity by HPLC:

EXAMPLE 4

Preparation of [N-Glutaryl(OFm)-(4-trans-L-Hyp)]-Ala-Ser-Chg-Gln-Ser-Leu-Dox Compound 3 (SEQ.ID.NO.: 2)

To a 3 necked, 12 L round bottom flask equipped with mechanical stirrer, thermocouple, and nitrogen inlet was charged DMF (5.1 L) and HOAt (43.4 g, 319 mmoles, 1.2 equivalents). The yellow solution was inerted with nitrogen and warmed to 40° C. Heptapeptide 1 (357.34 g, 266 mmoles) was added portion-wise to the warm solution; after stirring for 30 minutes at 40° C., a light yellow, opaque, homogeneous mixture resulted.

The mixture was cooled to room temperature, Doxorubicin 2 was added (158.9 g, 274 mmoles, 1.03 equivalents), and the red slurry was further cooled to −5° C. One equivalent of collidine (35 ml) was added followed by 0.8 equivalents of EDC (40.8 g, 213 mmoles) followed by the remaining two equivalents of collidine (70 ml). The red slurry was aged at −5° C. to −3° C.

The reaction was monitored by HPLC. After 1 hour, conversion had reached 58 A % Compound 3 and the remaining 0.5 eq. EDC (30.6 g, 160 mmoles) was charged.

After aging for a total of 3 hours, conversion had reached 90 A % Compound 3, 2.5 A % peptide 1 and the reaction was warmed to 0° C. Aging for another 2 hours reduced peptide level to 0.73 A % and the reaction was quenched as follows.

In a 50 L, 4 necked round bottom flask equipped with a mechanical stirrer, thermocouple, and nitrogen inlet, was charged $K_2HPO_4$ (67.9 g), $KH_2PO_4$ (283 g), and water (13 L) to give a 0.19 M pH 6.3 buffer solution. The buffer solution was inerted with nitrogen, cooled to 15–18° C., and the cold reaction mixture (−1° C.) was added to the buffer via an addition funnel over 60 minutes maintaining the slurry temperature at 15–18° C. After complete addition, the red slurry was aged 15 minutes at 18° C., and filtered. The filter cake was displacement washed with water (1×6 L), followed by slurry washing with water (6×6 L), and dried in vacuo at room temperature with a nitrogen sweep. After drying for 48 hours, a red solid with a TG. of 1.4% was obtained. The solid was analyzed by HPLC.

D-leucine Compound 3 Epimer assayed to 2.7 A %; the combined loss to the mother liquors and water washes was ca. 4%. No residual peptide was detectable; the residual doxorubicin level was 1.1 A %.

EXAMPLE 4A

Alternate Preparation of [N-Glutaryl(OFm)-(4-trans-L-Hyp)]-Ala-Ser-Chg-Gln-Ser-Leu-Dox Compound 3 (SEQ.ID.NO.: 2)

DMF (400 mL) was charged to a 1 L RB flask and degassed by $N_2$ sparge while cooling to −6° C. The peptide (19.97 g, 19.06 mmol) and HOAT (3.12 g, 22.9 mmol) were then charged as solids to the cold DMF. A slurry of doxorubicin-HCl (11.05 g, 19.06 mmol) in degassed DMF (50 mL) was charged by vacuum, followed by two rinses (2×25 mL) of the slurry flask. Collidine was charged followed by a portion of EDC (2.92 g, 0.8 eq.). After 1.3 h, a second charge of EDC (2.19 g, 0.6 eq) was made. After a total age of 7.4 h the clear red solution was queched by dropwise addition to a pH 6.2 phosphate buffer (1350 mL) at 16–17° C. over 1.3 h. The resulting slurry was filtered and the filter cake was then washed with water (2000 mL). The filter cake was dried under a $N_2$ stream giving 28.7 g red powder (95.6%, uncorrected for purity).

EXAMPLE 4B

Alternate Preparation of [N-Glutaryl(OFm)-(4-trans-L-Hyp)]-Ala-Ser-Chg-Gln-Ser-Leu-Dox Compound 3 (SEQ.ID.NO.: 2)

A 1 L, 4 neck round bottom flask was set up and 20.0 g of Doxorubicin.HCl (20.0 g, 34.5 mmol) was added in a glovebox. The flask was then equipped with a truebore stirrer, $N_2$ inlet/vacuum inlet, and a thermocouple. DMF (472 mL) and water (4.7 mL) were premixed (20° C.) and then charged to form a red slurry. The 2,4,6-collidine (12.5 g, 103 mmol) and 2-HOPO (4.6 g, 41.4 mmol) were then, respectively, charged at ambient temperature and allowed to mix for 10 minutes. The slurry was then cooled to −5° C. and the heptapeptide 2 (40.6 g, 35.3 mmol) was charged. It was stirred for 30 minutes at that temperature. The first, 0.8 equivalent of the EDC (5.3 g) was charged, and the solution allowed to mix for ~90 minutes. The reaction was monitored by HPLC.

After 90 minutes had elapsed, the remaining 0.6 equivalents of EDC (3.96 g) was added, the cooling bath was removed and the reaction was allowed to mix overnight at room temperature (21–22° C.).

The prepared buffer solution (1.20 L of the following buffer: 10.9 g $K_2HPO_4$, 43.54 g $KH_2PO_4$; pH 6.05) was added to a 3-L round bottom flask equipped with a truebore stirrer, $N_2$ inlet and thermocouple. The reaction solution was transferred to a 1-L addition funnel while, concurrently, the temperature of the buffer was reduced to 15–18° C.

The reaction solution was added to the buffer over 1–1.5 hours, while maintaining the temperature between 15–18° C. A precipitate resulted. The precipitated material was filtered and washed with water (2.30 L).

After drying overnight at 22° C. under $N_2$ and house vacuum, the solid (53.0 g) was assayed and was 91.5 A %, 88.1 wt. %. The yield after correction for purity was 86%.

EXAMPLE 4C

Alternate Preparation of [N-Glutaryl(OFm)-(4-trans-L-Hyp)]-Ala-Ser-Chg-Gln-Ser-Leu-Dox Compound 3 (SEQ.ID.NO.: 2)

A 3 L, 4 neck round bottom flask was set up and, concurrently, 20.0 grams of Doxorubicin.HCl (34.5 mmol) was added in a glovebox to a sealed beaker or Erlenmeyer flask. The 3 L flask was then equipped with a truebore stirrer, $N_2$ inlet/vacuum inlet, and a thermocouple. DMF (472 mL) and water (4.7 mL) were premixed (20° C.) and then partially charged (approximately ½ the volume) to the 3 L vessel. 2-HOPO (4.6 g, 41.4 mmol) and HOAt (0.47 g, 3.45 mmol) were then, respectively, charged and allowed to mix for 10 minutes or until dissolved. One-quarter of the wet DMF was then added to the doxorubicin.HCl to form a slurry, and this was then added to the 3 L vessel. Finally, the 2,4,6-collidine (12.5 g, 103 mmol) was added to the 3 L vessel which was then cooled to −5° C. and the heptapeptide 2 (40.6 g, 35.3 mmol) was charged. After stirring for 30 minutes the first 0.8 equivalents of the EDC was charged (5.3 g), followed by the final quarter of solvent. The resulting slurry was stirred for about 90 minutes and then the remaining 0.6 equivalents of EDC (3.96 g) was added. The cooling bath was removed and the reaction was allowed to mix overnight at room temperature (21–22° C.). Ethyl acetate (354 mL) was then added to the reaction solution at 20° C.

The temperature of the reaction solution was reduced to 15–18° C. The pH 6 buffer solution (1.20 L water, 10.9 $K_2HPO_4$, 43.54 g $KH_2PO_4$) was added slowly to the reaction solution over 1 hour, while maintaining the temperature between 15 and 18° C.

The precipitated material was filtered through a 600 mL medium sintered glass funnel, washed with water (2.3 L) and the cake was dried overnight on the filter at ambient temperature under $N_2$. The solid (54.5 g) was assayed at 89.7 A %. The yield, after correction for purity, was 90.0%.

EXAMPLE 5

Preparation of [N-Glutaryl-(4-trans-L-Hyp)]-Ala-Ser-Chg-Gln-Ser-Leu-Dox Piperidine salt Compound 4 (SEQ.ID.NO.: 1)

To a 3 necked, 12 L round bottom flask equipped with mechanical stirrer, thermocouple, and nitrogen inlet was charged Compound 3 (399 g, 253.5 mmoles, TG 1.4%) and DMF (3.55 L). The red solution was inerted with nitrogen, cooled to 1° C., and a solution of piperidine (40 mL, 404 mmoles, 1.6 eq.) in DMF (400 mL) was added drop-wise over 70 minutes maintaining the batch temperature at 0–2° C. The resulting purplish solution was aged under nitrogen at 0–2° C.

The reaction was monitored by HPLC. After aging 1.5 hours at 0–2° C., conversion had reached 92.4% [A % 4/(A % 4+A % 3)]. Additional piperidine was charged after 2 hours reaction time (2.5 mL piperidine in 25 mL DMF); after aging another 2 hours, conversion had reached 98.1% and the reaction was quenched as follows.

In a 22 L, 3 necked round bottom flask equipped with mechanical stirrer, thermocouple, and nitrogen inlet was charged isopropyl acetate (12.1 L), inerted with nitrogen, and cooled to 0–5° C. To the cold i-PAc was added the cold (2° C.) reaction mixture via nitrogen pressure cannulation over 40 minutes. The resulting pink slurry was aged at 0–5° C. for thirty minutes then filtered under nitrogen. The cake was displacement washed with i-PAc (2×4 L) then slurry washed with i-PAc (3×4 L). All washes were done under a nitrogen blanket. The solid was dried in vacuo at room temperature with a nitrogen sweep for 24 hours to give of an orange solid. The solid was assayed for purity using HPLC.

EXAMPLE 6

Preparative HPLC purification of [N-Glutaryl-(4-trans-L-Hyp)]-Ala-Ser-Chg-Gln-Ser-Leu-Dox Piperidinium salt/Free Acid Compound 4 (SEQ.ID.NO.: 1)

The crude piperidine salt was purified by preparative HPLC on C-18 silica gel, eluting with a 0.1% aqueous ammonium acetate/acetonitrile gradient (100% NH$_4$OAc to 55% NH$_4$OAc over 80 min). The rich cuts that were >97 LCAP pure were pooled to provide the purified salt.

A portion of the purified salt of Compound 4 was rechromatographed on C-18 silica gel using a 2% aqueous HOAc/acetonitrile gradient (100% aqueous HOAc to 40% aqueous HOAc over 60 min). The fractions that were >98 LCAP pure were pooled and lyophilized, providing the pure free acid 4.

EXAMPLE 7

Preparation of [N-Glutaryl-(4-trans-L-Hyp)]-Ala-Ser-Chg-Gln-Ser-Leu-Dox Sodium salt Compound 5 (SEQ.ID.NO.: 1)

The lyophilized Compound 4 free acid (2.0 g, 1.43 mmol), prepared as described in Example 5, was dissolved in 10 mL of water and a 0.100 N aqueous NaOH solution (14.3 mL, 1.43 mmol) was added over 10 min. with vigorous stirring. The pH of the solution at the end of the addition was 6.3. The water was removed by evaporation under a nitrogen stream to provide a microcrystalline solid.

Alternatively, addition of acetone to the aqueous solution of the sodium salt resulted in precipitation of the compound from solution. The salt was collected by filtration and dried under a nitrogen stream. The solid was recrystallized from 1:12 water:acetone to provide a microcrystalline solid.

EXAMPLE 8

Alternative Preparation of [N-Glutaryl-(4-trans-L-Hyp)]-Ala-Ser-Chg-Gln-Ser-Leu-Dox Sodium salt (Compound 5) (SEQ.ID.NO.: 1)

The compound 4 piperidine salt (10.37 g, 71% by wt free acid), prepared as described in Example 5, was dissolved in acetone (50 mL) and sodium acetate buffer (pH 5.2 0.2 M, 50 mL), and then stirred at 21–22° C. for 1 h. Acetone was then added (150 mL) slowly over 45 mins. The solution was then seeded with Compound 5 (50 mg) and the batch aged for 1 h at 21–22° C. Acetone (100 mL) was then added slowly over 2 h. The suspension was then cooled to 5° C. over 30 mins, and aged at 2–5° C. for 1 h. The product was isolated by filtration under an atmosphere of nitrogen, and the filter cake washed with 9:1 acetone/water (70 mL) followed by acetone (35 mL). The product was dried on the filter, under an atmosphere of nitrogen, overnight to give the sodium salt as a crystalline solid.

EXAMPLE 9

Alternative Preparation of [N-Glutaryl-(4-trans-L-Hyp)]-Ala-Ser-Chg-Gln-Ser-Leu-Dox Sodium salt (Compound 5) (SEQ.ID.NO.: 1)

Compound 3 (0.91 g) was added to a 250 mL three necked flask, and was dissolved in dry DMF (15 mL). The solution was degassed twice and then cooled to 0° C. 1.91 mL of the 1.0M piperidine in DMF was added over 60 minutes with a syringe pump. The solution was aged until disappearance of the Compound 3 was seen by HPLC (~125 min).

250 µL glacial acetic acid (6.9 eq) was then added over 10 minutes in order to keep the temperature below 5° C. 740 µL of 2 M NaOAc (2.33 eq) was then added to the solution.

Acetone (132 mL) was added slowly, however after addition of the first 30 mL a precipitate was seen. After addition of 50 mL of acetone, the mixture was seeded with 20 mg of Compound 5. The solution was aged for 30 minutes, and then the remaining acetone was added over 60 minutes, while maintaining the temperature below 5° C. The solid was filtered through a 60 mL medium sintered glass funnel, and the solid was washed with 10 mL 9:1 acetone-:water. It was allowed to dry with vacuum, with a nitrogen tent to provide Compound 5 as a solid.

EXAMPLE 9A

Alternative Preparation of [N-Glutaryl-(4-trans-L-Hyp)]-Ala-Ser-Chg-Gln-Ser-Leu-Dox Sodium salt (Compound 5) (SEQ.ID.NO.: 1)

Step 1: Preparation of crude [N-Glutaryl-(4-trans-L-Hyp)]-Ala-Ser-Chg-Gln-Ser-Leu-Dox Sodium salt (Compound 5) (SEQ.ID.NO.: 1)

To a stirred, cooled (−9° C.) solution of Compound 3 (20.7 mmol) in DMF (270 mL) was slowly added a solution of piperidine (62.1 mmol) in DMF (55 mL) over 8 min (−9 to −7° C.). The mixture was stirred at −10 to −5° C. over 3 h by which time HPLC assay showed the reaction to be complete (<1.0% Compound 3 remaining). The mixture was cooled to −10° C. and a mixture of glacial acetic acid (41.3 mmol) and 4–6M sodium acetate buffer (41.5 mmol) was added over 2 min (−10 to −7° C.). The mixture was stirred at −7 to −4° C. for 1 h and then acetone (325 mL) was slowly added at −5 to 0° C. over 30 min. The solution was seeded with sodium salt (0.3 g). Further acetone (1300 mL) was then added at −5 to 0° C. over 2 h. The suspension was stirred at 0° C. for 1 h and then the product was isolated by filtration under an atmosphere of nitrogen. The filter cake was slurry washed with 9:1 v/v acetone/water (200 mL) followed by acetone (200 mL). The solid was dried on the filter overnight under an atmosphere of nitrogen to afford crude sodium salt (31.00 g, 93.6 LCAP) in 85% assay yield and 12% assay yield lost to the combined liquors.

Step 2: Preparation of semi-pure [N-Glutaryl-(4-trans-L-Hyp)]-Ala-Ser-Chg-Gln-Ser-Leu-Dox Sodium salt (Compound 5) (SEQ.ID.NO.: 1)

A 1:1 v/v mixture of acetone: 0.2 M sodium acetate buffer (245 mL total volume) was prepared and added to Compound 5 (17.5 mmol). The mixture was stirred at ambient temperature until a clear solution was obtained (~0.5 h). Acetone (245 mL) was slowly added over approximately 80 min, and the solution then seeded with Compound 5 (0.2 g). A seed-bed was quickly established. Further acetone (122 ml) was then added slowly over 40 min, and the suspension stirred for 1 h at ambient temperature. Additional acetone was then added (245 mL) slowly over 1 h and the suspension cooled and stirred at 0 to 5° C. for 1 h. The product was then isolated by filtration under an atmosphere of nitrogen. The filter cake was washed with 9:1 v/v acetone/water (100 mL) followed by acetone (100 mL).

The product was dried on the filter overnight under an atmosphere of nitrogen to afford semi pure Compound 5 (26.73 g, 94.0 LCAP) in 91% assay yield and 5% lost to the combined liquors.

Step 3: Preparation of purified [N-Glutaryl-(4-trans-L-Hyp)]-Ala-Ser-Chg-Gln-Ser-Leu-Dox Sodium salt (Compound 5) (SEQ.ID.NO.: 1)

To a stirred solution of semi-pure Compound 5 from step 2 (15.9 mmol) in 1:1 v/v 2-propanol/0.2 M sodium acetate (222 mL) at ambient temperature was slowly added 2-propanol (183 mL) over approximately 30 min. The solution then seeded with Compound 5 (0.2 g). Further 2-propanol (150 ml) was then added slowly over 75 min. The suspension was stirred for 1 h at ambient temperature. Additional 2-propanol (222 mL) was then added slowly over 45 min and the suspension was cooled and stirred at 0 to 5° C. for 1 h. The product was then isolated by filtration under an atmosphere of nitrogen. The filter cake was washed with 9:1 v/v 2-propanol/water (100 mL) followed by 2-propanol (100 mL). The product was dried on the filter overnight under an atmosphere of nitrogen to afford purified Compound 5 (23.3 g, 89.7% 97.1 LCAP) in 94% assay yield and 6% assay yield lost to the combined liquors.

EXAMPLE 10

Lyophilized Formulation of [N-Glutaryl-(4-trans-L-Hyp)]-Ala-Ser-Chg-Gln-Ser-Leu-Dox (Compound 4) (SEQ.ID.NO.: 1)

The free acid compound 4 (40 mg), prepared as described in Example 6, was combined with 14 mg of trisodium citrate dihydrate and 100 mg of sucrose and dissolved in 1.0 mL of water. 0.1 N NaOH and 0.1 N HCl were added as needed to adjust the pH to 5.7. The solution was then lyophilized to provide a red cake.

EXAMPLE 11

Lyophilized Formulation of [N-Glutaryl-(4-trans-L-Hyp)]-Ala-Ser-Chg-Gln-Ser-Leu-Dox sodium salt (Compound 5) (SEQ.ID.NO.: 1)

The sodium salt compound 5 (40 mg), prepared as described in Examples 7–9, was combined with 14 mg of trisodium citrate dihydrate and 100 mg of sucrose and dissolved in 1.0 mL of water. 0.1 N NaOH and 0.1 N HCl were added as needed to adjust the pH to 5.7. The solution was then lyophilized to provide a red cake.

EXAMPLE 12

Alternative Lyophilized Formulation of [N-Glutaryl-(4-trans-L-Hyp)]-Ala-Ser-Chg-Gln-Ser-Leu-Dox sodium salt (Compound 5) (SEQ.ID.NO.: 1)

The sodium salt compound 5 (40.63 mg), prepared as described in Examples 7–9, was combined with 11.9 mg of trisodium citrate dihydrate, 1.50 mg of citric acid monohydrate and 100 mg of sucrose and dissolved in 1.0 mL of water. 0.1 N NaOH and 0.1 N HCl were added as needed to adjust the pH to 5.7. The solution was then lyophilized to provide a red cake.

What is claimed is:

1. A compound of the formula 5:

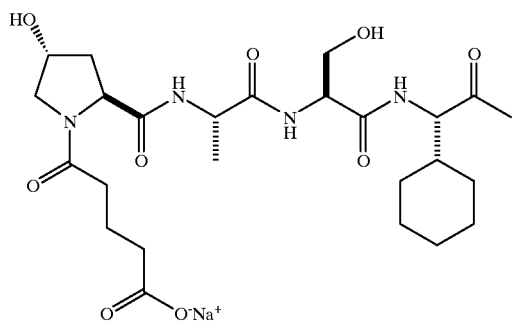

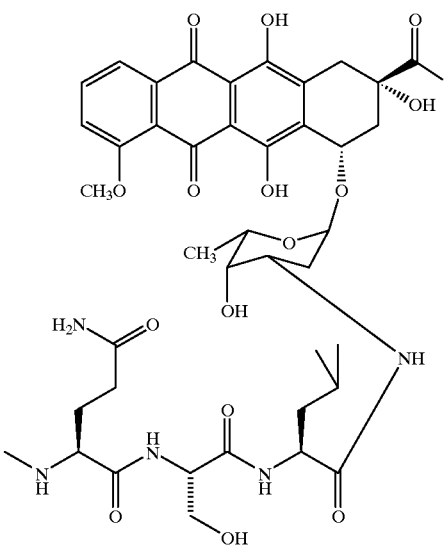

(SEQ.ID.NO.:1).

2. A pharmaceutical composition that comprises a pharmaceutical carrier, and dispersed therein, a therapeutically effective amount of the compound of the formula 5

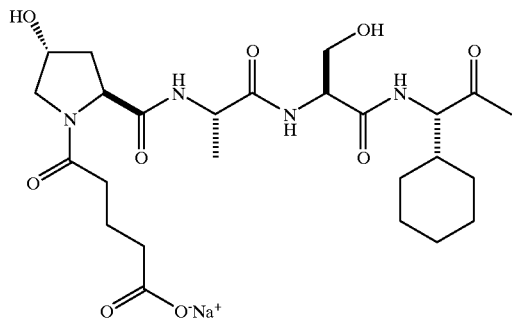

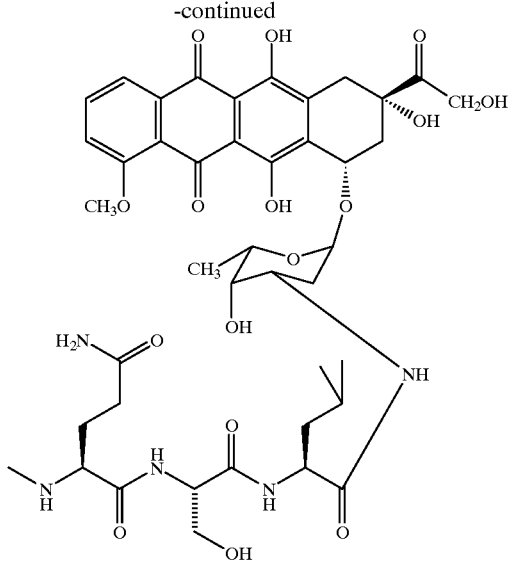

(SEQ.ID.NO.:1).

3. A method of treating prostate cancer which comprises administration to a mammal in need of such treatment a pharmaceutically effective amount of the composition according to claim 2.

4. A method of treating benign prostatic hyperplasia which comprises administration to a mammal in need of such treatment a pharmaceutically effective amount of the composition according to claim 2.

5. A process for the preparation of the compound of formula 5:

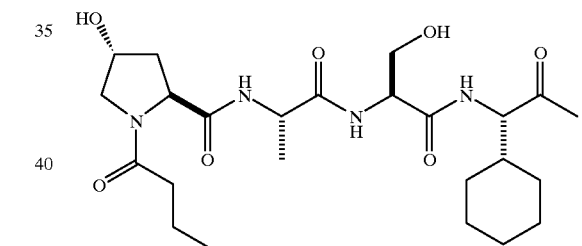

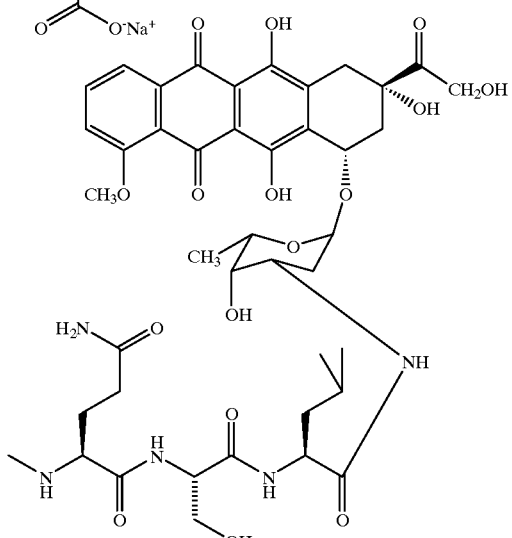

(SEQ.ID.NO.:1)

which comprises the step of mixing a PSA conjugate of the formula 4:

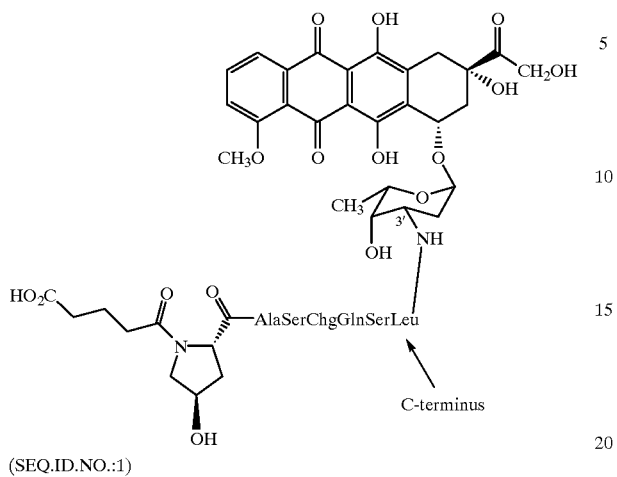

(SEQ.ID.NO.:1)

with a base that comprises: NaOH, Na$_2$CO$_3$, sodium acetate or sodium citrate.

6. The process according to claim 5 wherein the base is NaOH.

7. The process according to claim 5 wherein the base is sodium acetate.

8. A process for the preparation of the compound of formula 5:

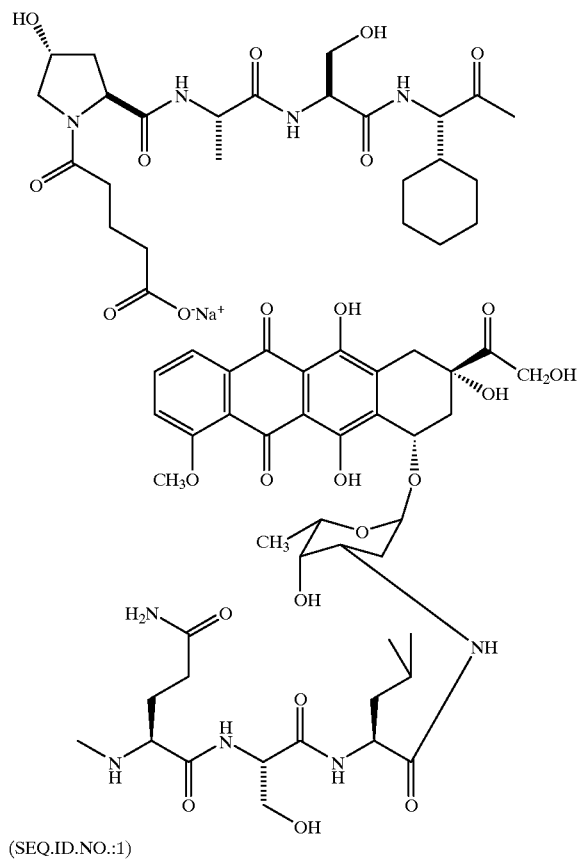

(SEQ.ID.NO.:1)

which comprises the step of mixing a piperidine salt of the PSA conjugate of the formula 4:

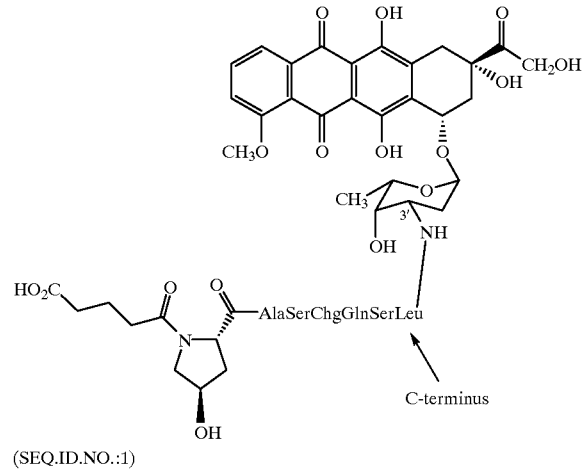

(SEQ.ID.NO.:1)

with a base that comprises: NaOH, Na$_2$CO$_3$, sodium acetate or sodium citrate.

9. The process according to claim 8 wherein the base is sodium acetate.

10. A process for the preparation of the compound of formula 5:

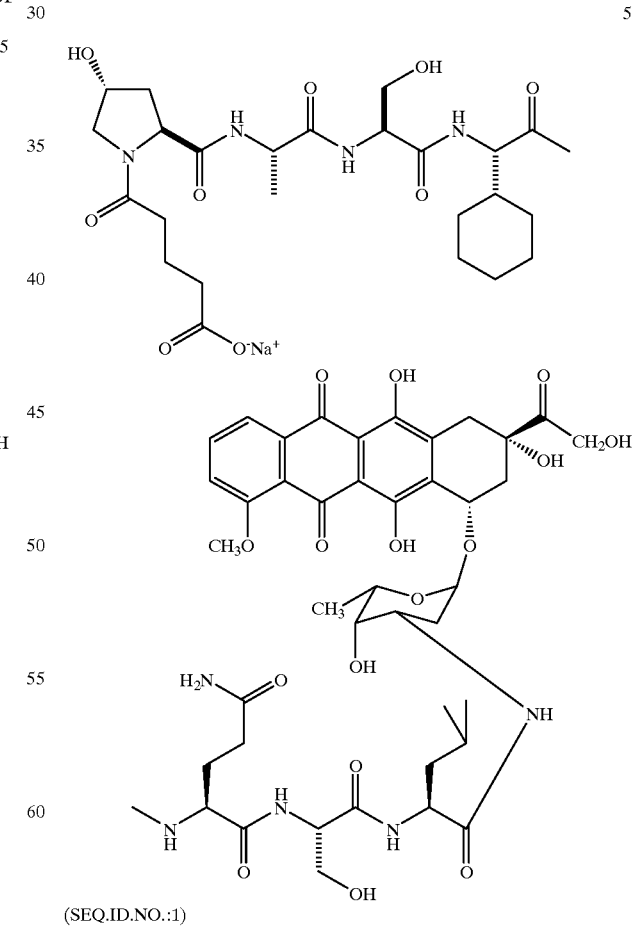

(SEQ.ID.NO.:1)

which comprises the steps of a) reacting the compound of the formula 3:

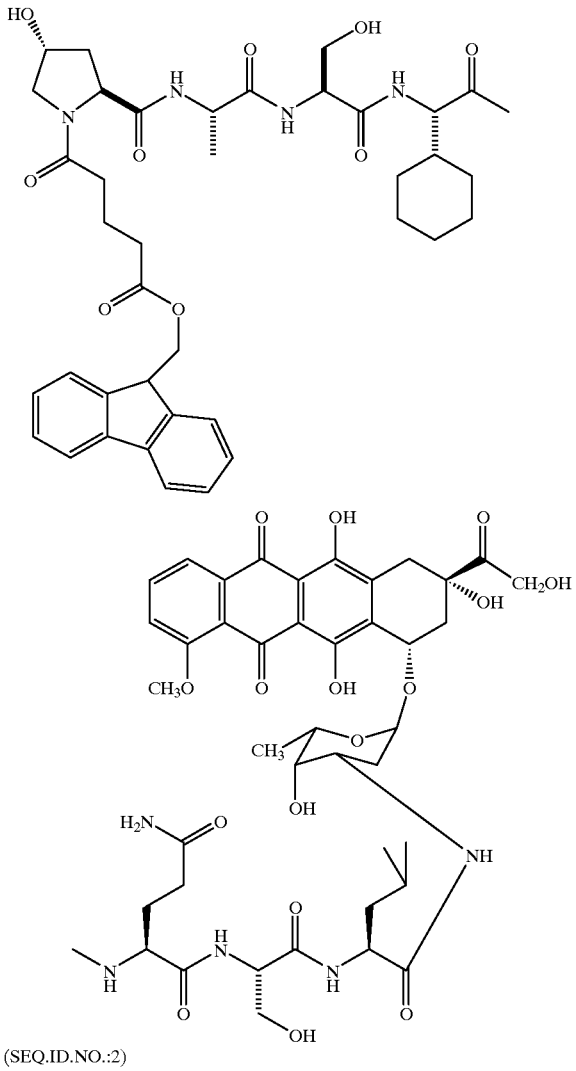

(SEQ.ID.NO.:2)

with piperidine to provide a resulting mixture;

b) treating the resulting mixture with an acid to provide a second resulting mixture; and treating the second resulting mixture with a base;

wherein the base comprises: NaOH, $Na_2CO_3$, sodium acetate on sodium citrate.

11. The process according to claim 10 wherein the base is sodium acetate.

12. The process according to claim 10 wherein the acid is selected from the group consisting of: hydrochloric acid and acetic acid.

13. The process according to claim 12 wherein the acid is acetic acid.

14. A lyophilized formulation comprising a compound of the formula 4

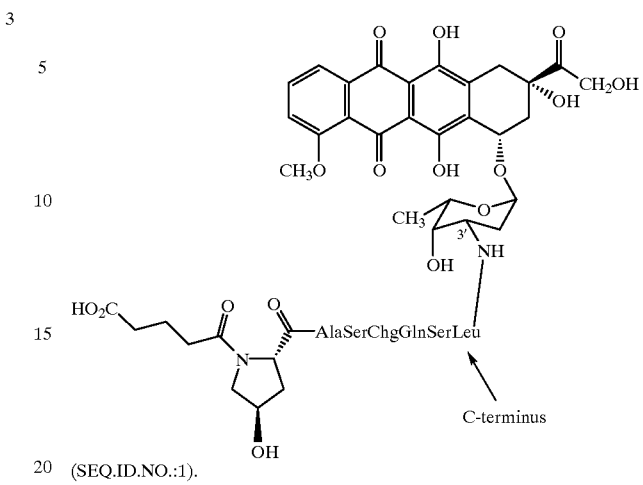

(SEQ.ID.NO.:1).

and a carboxylate salt.

15. The lyophilized formulation according to claim 14 wherein the carboxylate salt is selected from acetate, ascorbate, benzoate, citrate, formate, fumarate, lactate, maleate, malate, succinate, tartrate-α and tartrate-m.

16. The lyophilized formulation according to claim 15 wherein the carboxylate salt is selected from citrate, succinate, tartrate-α and tartrate-m.

17. The lyophilized formulation according to claim 16 wherein the carboxylate salt is trisodium citrate.

18. The lyophilized formulation according to claim 14, which further comprises a sugar.

19. The lyophilized formulation according to claim 18, wherein the sugar is selected from glucose, mannitol, lactose, sucrose and fructose.

20. The lyophilized formulation according to claim 17, wherein the sugar is sucrose.

21. A lyophilized formulation prepared by combining a compound of the formula 4

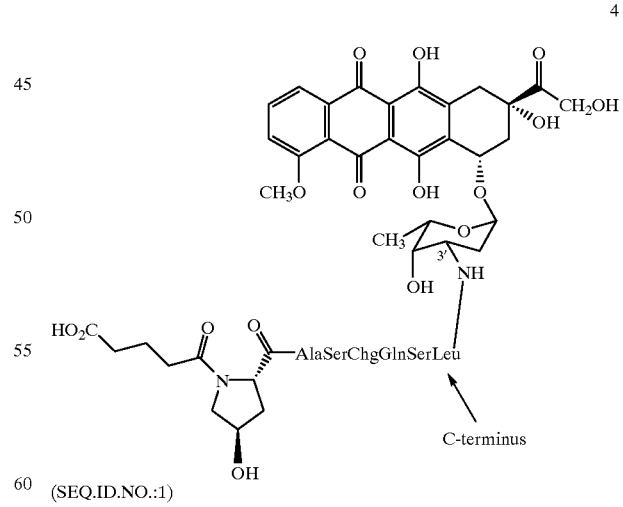

(SEQ.ID.NO.:1)

with a carboxylate salt.

22. The lyophilized formulation according to claim 21 wherein the carboxylate salt is selected from acetate, ascorbate, benzoate, citrate, formate, fumarate, lactate, maleate, malate, succinate, tartrate-α and tartrate-m.

23. The lyophilized formulation according to claim 22 wherein the carboxylate salt is selected from citrate, succinate, tartrate-α and tartrate-m.

24. The lyophilized formulation according to claim 23 wherein the carboxylate salt is trisodium citrate.

25. A lyophilized formulation comprising a compound of the formula 5

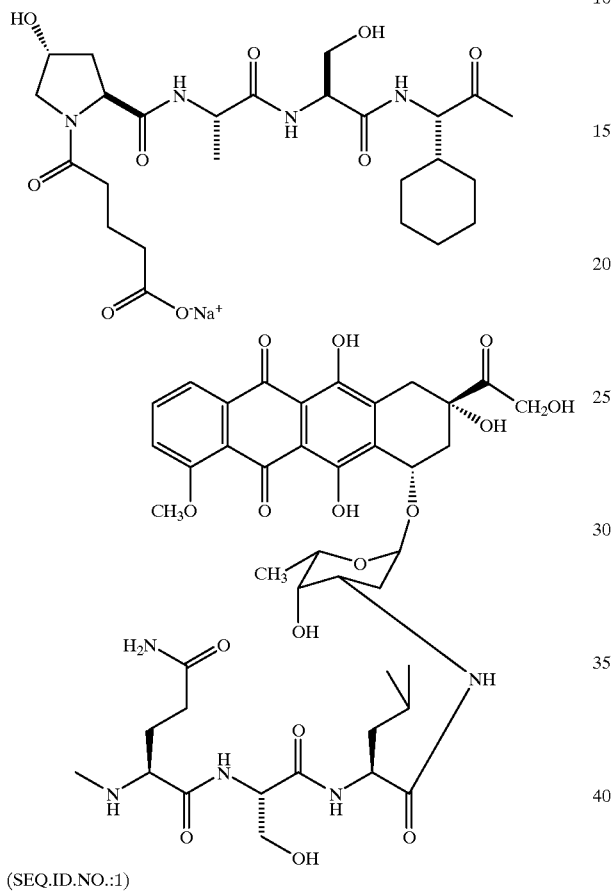

(SEQ.ID.NO.:1)

and a carboxylate salt/carboxylic acid buffer.

26. The lyophilized formulation according to claim 25 wherein the buffer is selected from trisodium citrate/citric acid buffer, disodium succinate/succinic acid buffer or sodium tartrate/tartaric acid buffer.

27. The lyophilized formulation according to claim 26 wherein the buffer is trisodium citrate/citric acid buffer.

28. The lyophilized formulation according to claim 25, which further comprises a sugar.

29. The lyophilized formulation according to claim 28, wherein the sugar is selected from glucose, mannitol, lactose, sucrose and fructose.

30. The lyophilized formulation according to claim 29, wherein the sugar is sucrose.

31. A lyophilized formulation prepared by combining a compound of the formula 5

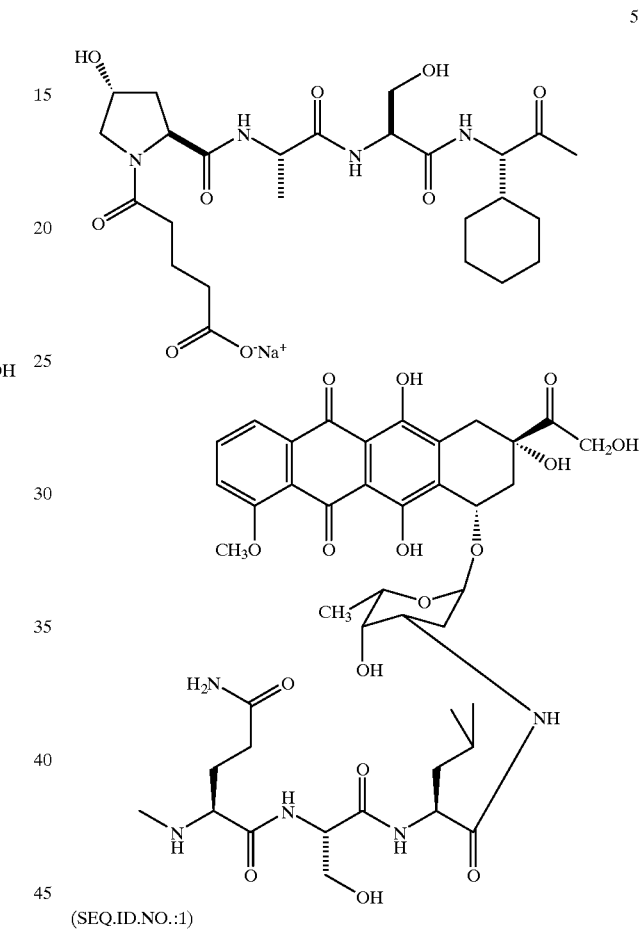

(SEQ.ID.NO.:1)

and a carboxylate salt/carboxylic acid buffer.

* * * * *